United States Patent [19]

Taylor et al.

[11] Patent Number: 5,047,025

[45] Date of Patent: Sep. 10, 1991

[54] THERMAL ATHERECTOMY DEVICE

[75] Inventors: James M. Taylor, Mountain View, Calif.; David F. Wirt, Prescott, Wis.

[73] Assignees: Metcal, Inc., Menlo Park, Calif.; Minnesota Mining and Manufacturing Company, St. Paul, Minn.

[21] Appl. No.: 464,399

[22] Filed: Jan. 12, 1990

[51] Int. Cl.$^5$ .............................................. A61B 17/36
[52] U.S. Cl. .......................................... 606/31; 606/28
[58] Field of Search ....................... 606/27, 28, 29, 30, 606/31, 7

[56] References Cited

U.S. PATENT DOCUMENTS

| | | | |
|---|---|---|---|
| 3,903,891 | 9/1975 | Brayshaw | 606/27 |
| 4,627,436 | 12/1986 | Leckrone | 606/7 |
| 4,643,186 | 2/1987 | Rosen | 606/33 |
| 4,654,024 | 3/1987 | Crittendon | 606/31 |
| 4,672,962 | 6/1987 | Hershenson | 128/401 |
| 4,685,458 | 8/1987 | Leckrone | 606/7 |
| 4,748,979 | 6/1988 | Hershenson | 128/401 |
| 4,760,845 | 8/1988 | Kovalcheck | 606/28 |
| 4,790,311 | 12/1988 | Ruiz | 606/28 |
| 4,807,620 | 2/1989 | Strul | 606/28 |
| 4,899,741 | 2/1990 | Bentley | 606/27 |

FOREIGN PATENT DOCUMENTS 1284528 12/1968 Fed. Rep. of Germany ........ 606/27

OTHER PUBLICATIONS

Electrical Thermal Angioplasty: Catheter Design Features, In Vitro Tissue Ablation Studies and In Vivo Experimental Findings, David Y. Lo et al., American Journal of Cardiology, Nov. 1, 1987, pp. 1117-1123.

Primary Examiner—Kyle L. Howell
Assistant Examiner—Robert L. Nasser, Jr.
Attorney, Agent, or Firm—Howard L. Rose

[57] ABSTRACT

A catheter is provided with a heated temperature self regulating tip for insertion in an artery to ablate an atherosclerotic plaque obstruction particularly in coronary and peripheral arteries. The heater is located at the distal end of the catheter and has a winding of fine wire around a ferro-magnetic core with the wire being connected via a transmission line to a high frequency constant alternating current source in the megahertz range. The catheter which may or may not employ a guide wire is inserted into and through the lumen of a vessel and guided usually with the assistance of fluoroscopy to the location of the stenosis. The heater is energized to ablate the plaque, the temperature not exceeding a desired temperature as determined by the Curie temperature of the ferromagnetic material.

10 Claims, 3 Drawing Sheets

THERMAL ATHERECTOMY DEVICE

FIELD OF THE INVENTION

The present invention relates to catheters and the like and more particularly to steerable, heated catheters for removing atherosclerotic plaque from coronary as well as peripheral arteries.

BACKGROUND OF THE INVENTION

Atherosclerotic plaque is a relatively common occurrence in these times of rich foods and long life. The plaque produces a stenosis reducing the diameter of the lumen of the artery and restricting blood flow to the region beyond the stenosis. In some instances a balloon catheter may be employed to increase the diameter of the lumen particularly where complete blockage of the artery has not occurred and the plaque has not become calcified or otherwise hardened. In those instances where a balloon catheter cannot be used or cannot be used initially, catheters may be used to bore through the plaque and increase the diameter of the lumen through the stenosis.

The use of steerable catheters to remove atherosclerotic plaque both from coronary as well as peripheral arteries is in increasing use today. In the art today, there are heated catheters, cutting blade catheters and laser catheters all of which may be quite dangerous in use since, if aimed incorrectly or overheated, they can damage the wall of an artery producing serious, if not fatal, injury or cause particles to enter the blood stream.

Various approaches to reducing these hazards have been suggested. Very thin guide wires may be employed to facilitate guiding the catheter to the proper location. With lasers, optical fibers may be employed to conduct the laser energy to the site rather than feed the laser through the arteries whereby to better control various factors such as aim of the beam and the energy supplied by the laser.

Various of these techniques are being employed today but danger of overheating and misdirection are still prevalent although the use of guide wires has materially reduced the danger of mechanical puncture of the wall of an artery. The problem of overheating or of elaborate controls to prevent overheating are still prevalent. Further, there is the danger that solid or liquified plaque may enter the blood stream and produce serious blockage, particularly in small coronary arteries.

BRIEF DESCRIPTION OF THE PRESENT INVENTION

In accordance with the present invention there is provided a catheter with a heated tip for use in removing atherosclerotic plaque in coronary and peripheral arteries, which catheter has a temperature self regulating heater built into its tip. Preferably the catheter operates in conjunction with a guide wire so as to be guided along the wire to the location of the stenosis. A fine guide wire can be more readily manipulated than a catheter and, as such, greatly reduce the danger of entering the wrong artery or puncturing the wall of an artery. The catheter can be easily slid along the guide wire to the desired location.

In the present invention the use of the guide wire in conjunction with a temperature self regulating heater removes the most common dangers in the use of such instruments. The use of the guide wire is not essential but when the catheter is constructed such as to be usable with a wire, the margin of safety is greatly increased.

The present invention employs a temperature self regulating heater, with regulation of temperature being accomplished by employing a high mu material such as a ferromagnetic, ferrimagnetic or the like material having a Curie temperature at the desired maximum temperature of operation. As pointed out in U.S. Pat. No. 4,256,945 a ferromagnetic conductor connected in series in a circuit having a high frequency, constant current supply regulates temperature up to and about the effective Curie temperature of the ferromagnetic conductor. The effective Curie temperature is that at which the material becomes essentially paramagnetic for purposes of operation of the heater. Such temperature may however be a few or as much as 100 degrees less than absolute Curie temperature where the material becomes truly paramagnetic.

The high mu material, hereinafter "heater", increases in temperature until the effective Curie temperature is approached. At this time the resistance of the heater decreases and, since current is constant and thus $I^2$ is constant ($K = I^2$), the power dissipation is controlled by the equation: $P = KR$. The reduction in resistance causes a reduction of power dissipation and thus in temperature until the heater material again enters the high mu range, preferably an effective mu of 100 or more and the heating cycle starts again.

The above operation is also basically true in a flux coupled heater where the high mu material is subject to a high concentration of magnetic flux causing the material to heat. Upon approaching Curie temperature, the material becomes generally paramagnetic so that the flux coupling is greatly reduced and the heater cools until high mu properties are restored.

The temperature of the device at the stenosis must be such as to ablate the plaque by vaporization, thus preventing pieces of the plaque or melted plaque from entering the blood stream. Also the design of the structure must be such that at such a temperature minimal damage is done to the walls of the artery. The Curie temperature of the high mu material is the maximum temperature of the device which, in practice, is not often achieved but is approached when the stenosis is engaged and blood is essentially excluded from the region of contact. The operating temperature range of the various Curie temperature materials employed in conjunction with the structure described below is a function of the environment in which employed. It has been found that at a heater Curie temperature of about 300° C. the catheter will tend to stick to the walls of the vessels. Materials having Curie temperatures of 450° C. to approximately 620° C. have been tried, the latter permitting not only a more rapid procedure but decreasing the margin of thermal damage to the walls of the arteries. Thus the Curie temperature selected is a compromise between the utility and safety of a rapid procedure and the apparent safety of lower temperatures.

The present invention contemplates an atherectomy catheter preferably movable along a guide wire for purposes of removing plaque from coronary and peripheral arteries. The size of the catheter described herein is employable in peripheral and the larger coronary arteries. In most instances the tip for use in peripheral arteries comprises a hollow, cylindrical body of, for instance, a ferromagnetic material having a flared head at one end of the cylinder. A collar is located adjacent the other end of the hollow cylindrical tip and wire is wound helically in several layers about the cylindrical body between the head and the collar. Various coatings are applied over the wire until a smooth transition exists between the head and collar. In the embodiment disclosed herein the maximum diameter of the catheter is at the location of the collar. The maximum diameter of the device varies with intended use and typically in conjunction with peripheral arteries may vary from 0.040 to 0.160 inch.

The helically wound wire is brought out through a slot in the collar and is connected to a coaxial cable. A tube which carries a guide wire to the interior of the hollow cylindrical tip is encased, along with the coaxial cable, in an outer casing which, depending upon use, may or may not be enclosed within a spiral spring.

The use of a center core of high mu material with a larger head and the coil wound about the core behind the head insures that the head achieves maximum temperature while the walls of the artery are shielded from maximum temperature by the coil and the coatings around the wire. The only region of the device that develops maximum temperature and contacts the wall of the artery is the very short edge of the head and thus thermal damage is held to minimal levels. Also, the slight taper of the device inwardly toward the head end tends to keep maximum heat away from the wall.

In use, entry is made into an artery that leads to the artery to be treated. A guide wire is inserted through the entry into the artery and while being observed by fluoroscopy is guided to the stenosis. Once the guide wire is across the stenosis, the catheter is advanced over the guide wire until it reaches the stenosis. The coaxial cable may then be attached to an appropriate power supply and the heater energized by magnetic coupling to the coil.

The heater to be described herein is operated at about 13.56 MHZ and has an effective Curie temperature preferably in a range of 450° C. to 620° C. The frequency of operation may vary depending upon size of the device, materials employed and the like may vary from 10 MHz to 2 GHz. The construction is such that at a given frequency the conversion of input of electrical energy to heat energy is maximized. The wattage of the power supply must be sufficient to cause the heater temperature to approach Curie temperature rapidly and to have Curie temperature rapidly re-established in the presence of a sudden change in thermal load. Since the environment in which the various heaters will be employed varies with their use and thus a fixed figure is not possible, it appears that 18–42 watts at 13.56 KHz is sufficient. Although 18 watts does not seem very great the energy is so concentrated that the heater can produce a localized third degree burn in water in less than one second.

It is thus a primary object of the present invention to provide a small, temperature self regulating, heated tip catheter for use in removing plaque from arteries of humans and animals, which catheter may be employed with a guide wire and which minimizes danger to the walls of the arteries.

DETAILED DESCRIPTION OF THE PRESENT INVENTION

Figure 1:
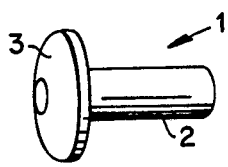
FIG. 1 illustrates the core and tip of the catheter.

Referring now specifically to FIG. 1 of the accompanying drawings, there is illustrated the hollow core and tip 1 of the catheter fabricated from high mu material, which term includes ferromagnetic, ferrimagnetic and like material. The core and tip include a hollow cylindrical body 2, the core, terminating at one end in an enlarged round head 3 coaxial with the cylindrical body 2. The center bore of the tip 1 should accommodate a 0.016 inch guide wire.

Figure 2:
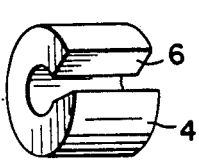
FIG. 2 illustrates the collar employed in the catheter.
Figure 3:
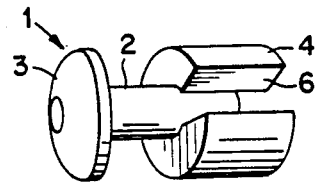
FIG. 3 illustrates the tip and collar assembled.
Figure 4:
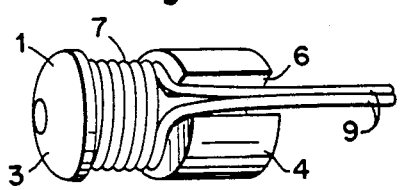
FIG. 4 illustrates the assembled tip and collar with the heater winding wound about the tip.

A collar 4 of low mu material is illustrated in FIG. 2. The collar 4 is a hollow cylinder having a slot 6 extending parallel to the axis of the collar for purposes to be described. The interior dimension of the collar 4 is such as to snugly receive the end of the cylindrical body 2 to which it is secured, by welding for instance, by anchor wire 21; see FIG. 6. A wire is wound about the body 2 to form a coil 7 with its ends 9 brought out through the slot 6 in the collar; FIG. 4.

In one embodiment, the tip 1 is fabricated from a Type 430 stainless supplied by Carpenter Steel Division of Cartech. The collar 4 is fabricated also by the Carpenter Steel Division of Cartech. The material is a Type 304 stainless. The wire is 0.27% nickel clad high temperature copper wire.

Figure 5:
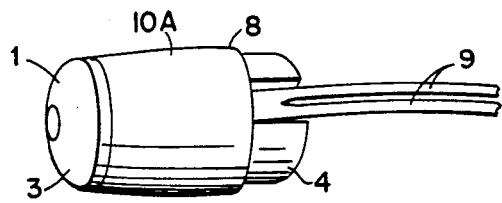
FIG. 5 illustrates the completed tip, collar and winding assembly.

Referring now to FIG. 5 of the drawings, the space between the head 3 and the collar 4 is partially filled with a dielectric cross-over paste from Transene Company, Inc., Type 1500 which in turn is mixed with any one of several different types of bio-compatible glasses 10A to provide a smooth transition between the head and the collar 4. The inward taper of the head is roughly 5° from back to front. Some of the cross-over paste is disposed in the slot 6 of collar 4 to secure the wires in the slot. The specific materials currently employed are TGC-120 glass (a lead borosilicate glass) mixed 50/50 by weight with a dielectric cross-over paste (basically alumina powder mixed with cellulose) in a carbotol acetate solvent to render the material workable. The material is applied in layers and is baked in between to dry out the material. These materials may be replaced with comparable materials in the future. A tapered head is preferable but in some instances a non-tapered head may be employed.

Figure 6:
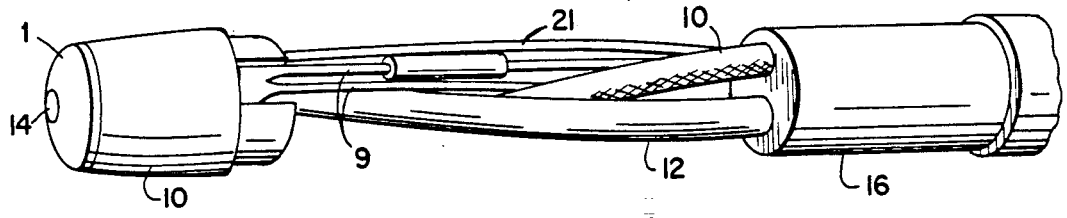
FIG. 6 illustrates the initial connections of the assembly of FIG. 5 in a cable connected to the external components of the device.
Figure 7:
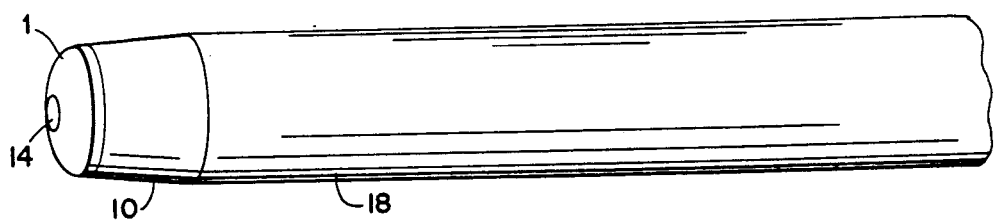
FIG. 7 illustrates the completed connection of the tip assembly to the cable.
Figure 8:
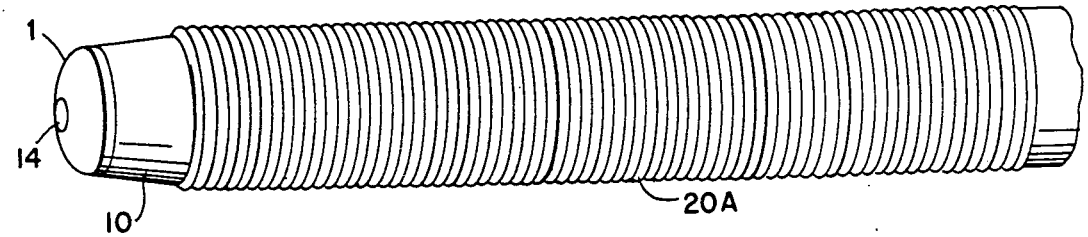
FIG. 8 illustrates the application of a spiral external spring to the assembly of FIG. 7.

Referring now specifically to FIG. 6 of the accompanying drawings, one of the wires 9 is connected to the center conductor of a coaxial cable 10, that serves as a transmission line, while the other wire 9 is connected to the braid of the cable 10. A hollow tube 12 has one end aligned with axial passage 14 through the tip 1. The tube extends to the end of the cable structures as discussed relative to FIG. 9 and is adapted to receive a guide wire which may pass through the tube 12 and into and through the passage 14 in the tip 1. The coaxial cable 10 and tube 12 extend through a flexible body 16, which may be polyurethane, to the remote end of the instrument. An anchor wire 21 to prevent loss of the distal end of the catheter is secured to the core 2 and extends through the flexible body 16 to a four-port-Y 20, see FIG. 9, where it is anchored. The region between the rear of the core 2 and the body 16 is potted, a typical potting material being a Type A medical, adhesive silicon. PTFE (polytetrafluoroethylene) sleeve 18 (FIG. 7) extends from the rear of the tip (collar) to the distal shoulder of the flexible body 16 to complete construction thereof. If desired in a particular application, an elongated spiral spring 20A (FIG. 8) may be disposed about the catheter from adjacent the collar 4 to a region beyond the beginning of tube 12.

At the end of the cable 16 remote from the catheter tip 1, three members are brought out, the tube 12, the coaxial cable 10 and a further member 30 which is employed to insert fluoroscopic dye into the tube 12.

Figure 9:
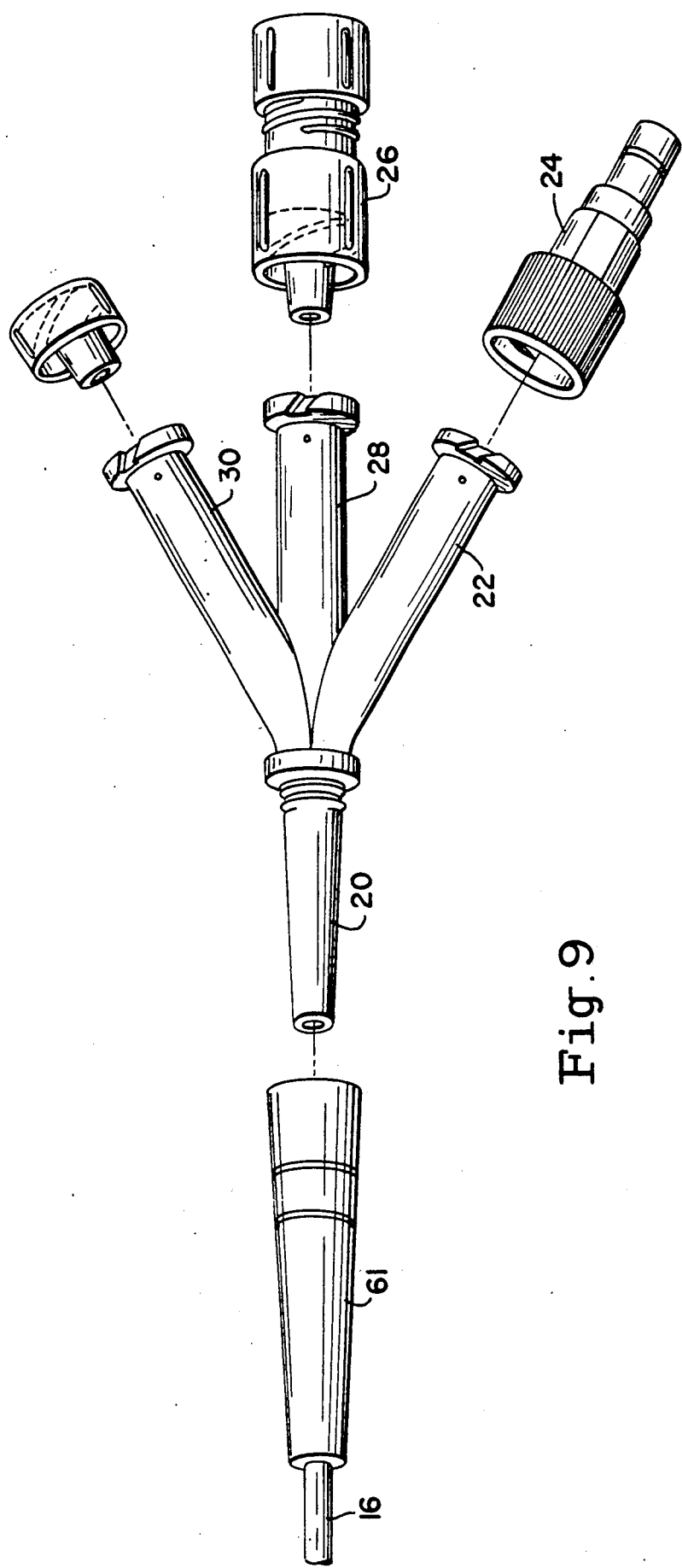
FIG. 9 illustrates the members involved in the connections of the cable to the external components of the system.

Referring now to FIG. 9, there is illustrated an exploded view of the connections to the cable 16 at the end remote from the head 3. The cable 16 passes through a sleeve 61 of flexible material employed to protect the end of the cable. Secured inside of the sleeve is a "four-port Y" 20 internally of which the cable 16 ends. The coaxial cable, covered in TEFLON (ATFE), is brought out through sleeve 28 to a coaxial connector 26. A guide wire is inserted through an adapter 24 and sleeve 22 into the interior of the four-port Y where it enters cable 16 and eventually tube 12. A further sleeve 30 is adapted to receive a fluoroscopic dye and transmit it to the interior of the four-port Y 20 where it enters cable 16, tube 12 and is eventually inserted into the artery through tip 1 and possibly through side holes in cable 16 for obvious purposes.

In use, a guide wire, if one is employed, is inserted into an artery and guided to the location of the stenosis. The hot tip catheter is then threaded onto the wire at its end external to the patient's body and slid along the wire until it reaches the stenosis. The heater is then activated and brought into contact with the stenosis to ablate the plaque to either create a passage through the plaque or to widen an existing passage whereby in either event to increase blood flow through the affected region. The procedure may, under appropriate circumstances, substantially clear the blockage or produce a passage large enough to permit balloon angioplasty.

As previously indicated there are two main concerns relating to catheters employed primarily to remove atherosclerotic plaque from human arteries. These concerns relate first to minimizing introduction of liquified plaque and or pieces of plaque into the blood stream and seconded damage to the arterial walls. The present device accomplishes both of these purposes by employing high mu materials that operate at temperatures that ablate the plaque so that it is absorbed into the blood in gaseous form thus minimizing the dangers incident to its removal. Acceptable ablation temperatures lie in the range of approximately 450° C. to 620° C. and specifically above 300° C. at which temperature the catheter may stick to the walls of the artery.

The second concern relates to damage to the walls of the artery due to excessive heat. By employing a structure where the heat is generated at the front center of the tip 1, and surrounding the core with a coil and the coil with materials that are poor heat conductors, the sides of the tip 1 are maintained at a temperature below that of the core and the head 3; the latter being a direct extension of the core. The heat employed to ablate the plaque is primarily dissipated at the head 3 and is thus applied primarily to the plaque as opposed to the arterial walls.

Figure 10:
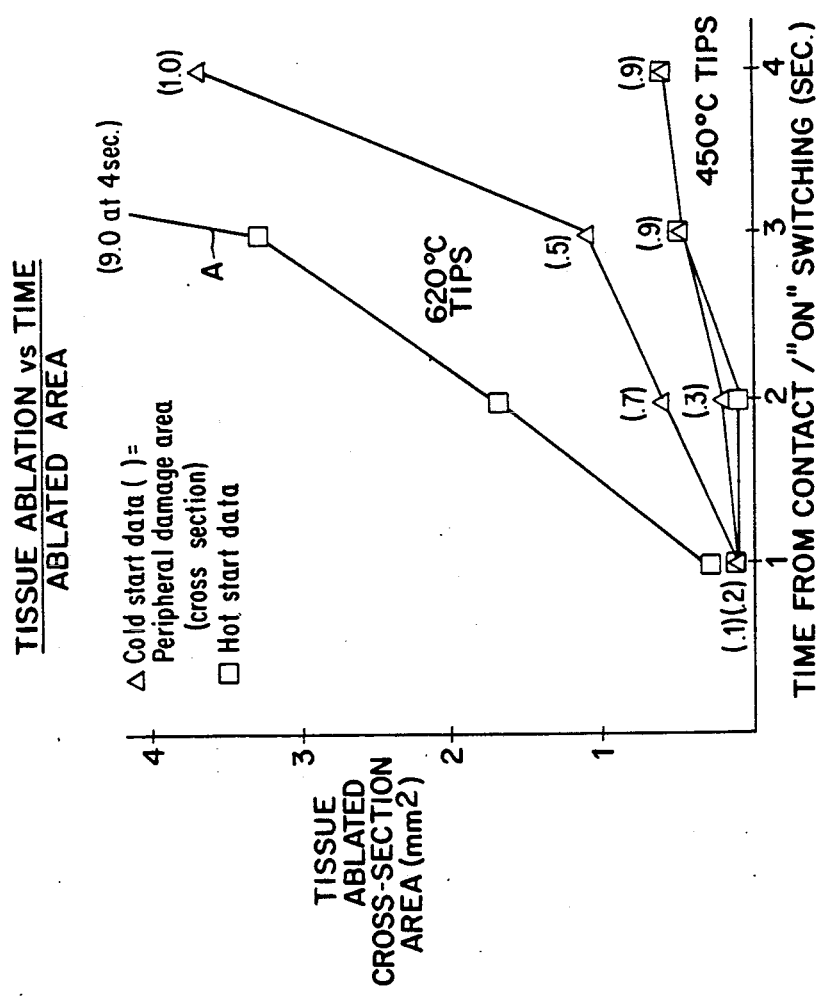

Referring specifically to FIG. 10 of the accompanying drawings, there is a graph of the tissue ablation of the present catheter as a function of time, for heaters having Curie temperatures of 450° C. and 620° C. It is readily noted that the higher Curie temperature catheter ablates tissue at a far greater rate. The peripheral (wall) damage margin (cross-sectional area) is given in parentheses at each of the graph points. Damage for Graph A after 3 seconds is 0.7 mm$^2$, an acceptable margin, roughly equivalent to that caused by a scalpel blade.

It is apparent that the greater the power available to the tip, the faster it will rise to temperature and hold temperature in the face of changing, specifically, increasing load. The load varies greatly with the rate at which it is attempted to move the catheter through a blockage so that the more power that is available the more uniform the temperature will remain and the more quickly can the catheter be moved. As in any invasive procedure, it is most desirable to go in and get out as quickly as is commensurate with safe procedures.

Figure 11:
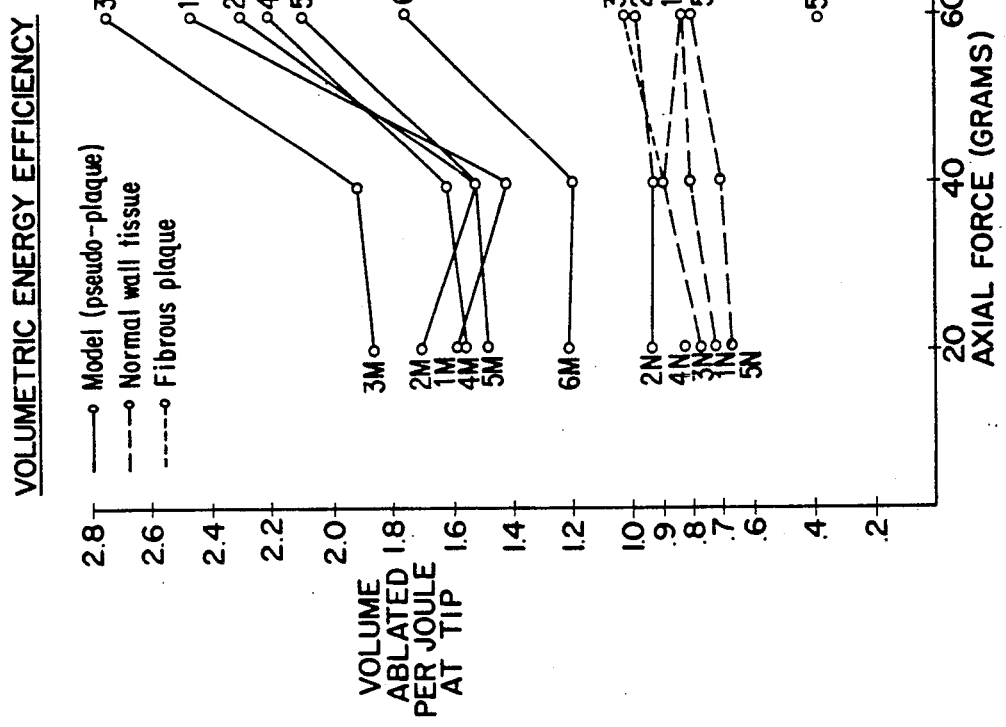
FIG. 10 comprises a series of graphs illustrating tissue ablated versus time for catheters of two different Curie temperatures and
FIG. 11 is a series of graphs illustrating ablation rate per unit energy as a function of axial force for a series of prototype catheters having various heater and overall diameters (No. 3 values approximate described device).

Referring to FIG. 11 of the accompanying drawings the ablated volume is plotted as a function of axial force in grams for three different types of "blockage" materials. The numerical designations are: 1 and 2 discontinued models, 3 is an 80 thousandth diameter heater, 4 is a 60 thousandth diameter heater, 5 is a 70 thousandth diameter heater and 6 failed. The model (pseudoplaque) is polyurethane gel of 90% water.

The term "constant current" as used herein refers to a current, I, where:

$$\frac{\Delta |I|}{I} < -1/2 \frac{\Delta |R|}{R}$$

The degree of self regulation is a function of the differences in degree of change of the two sides of the equation. If $\Delta |I|$ is equal to zero good regulation is achieved as set forth in U.S. Pat. No. 4,256,945. As the value of the left side of the equation approaches that of the right side, the degree of self regulation decreases. The power supply used may be any one of the supplies described in U.S. Pat. Nos. 4,626,767, 4,752,864, 4,795,886 or 4,769,519 or other controlled current power supplies available on the market that can produce frequencies in the megacycle range. The first two supplies mentioned above by patent number operate at 13.56 MHZ, preferably.

Many variations and modifications of the above-described embodiments are within the ordinary skill of the skilled artisan in this art, without departing from the scope of the invention. Accordingly, those modifications and embodiments are intended to fall within the scope of the invention as defined by the following claims:

We claim:

1. A thermal atherectomy device comprising
   a tip of high mu material having a round head and elongated cylinder of smaller diameter than said head extending axially therefrom,
   an axially slotted collar secured to said cylinder remote from said head,
   a coil of wire wound about said cylinder between said head and said collar and having its end sections extending through said slot in said collar,
   a smooth coating of low heat conductive material covering said coil, and
   means for connecting said coil of wire to a high frequency source of alternating current.

2. A thermal atherectomy device according to claim 1 wherein said tip has an aperture therethrough coaxial with said head and said cylinder.

3. A thermal atherectomy device according to claim 2 further comprising a hollow tube communicating with said passage, and
   wherein said means includes a coaxial cable connected to said coil and connectable to a source of constant current.

4. A thermal atherectomy device according to claim 1 adapted for thermal angioplasty wherein the transmission line is constructed and arranged to pass through a blood vessel so that the occlusive effect of plaque residing within the vessel may be reduced.

5. A thermal atherectomy device according to claim 1 wherein said tip tapers inwardly from said collar toward said head.

6. A thermal atherectomy device according to claim 1 wherein said taper is approximately 5°.

7. A thermal atherectomy device comprising
   a tip of high mu material having a round head and a coaxial cylindrical extension of lesser diameter,
   an electrically conductive coil of wire wound about said cylindrical body to a diameter less than the diameter of said head,
   means for connecting said coil of wire to a source of electrical power to heat said tip to a temperature approaching its effective Curie temperature,
   a mixture of a glass and a dielectric crossover paste disposed over said coil to the maximum diameter of said head adjacent said head and tapered outwardly along said cylinder.

8. A thermal atherectomy device according to claim 7 wherein a hole extends through said tip coaxial with said cylinder and head.

9. A thermal atherectomy device according to claim 7 further comprising;
   a collar coaxial with and disposed about said cylinder remote from said head;
   said collar having a slot through which the wires at the ends of the coil extend,
   said slot also being filled with said adhesive and said coating.

10. A thermal atherectomy device according to claim 9 wherein said collar defines the maximum diameter of said device.

* * * * *